US007625744B2

(12) United States Patent
Van Der Meer (10) Patent No.: US 7,625,744 B2
(45) Date of Patent: Dec. 1, 2009

(54) BIOLOGICALLY BASED TEST SYSTEM (75) Inventor: Jan Roelof Van Der Meer, Dübendorf (CH)

(73) Assignee: Helmholtz-Zentrum für Umweltforschung GmbH-UFZ, Leipzig (DE)

( * ) Notice: Subject to any disclaimer, the term of this patent is extended or adjusted under 35 U.S.C. 154(b) by 557 days.

(21) Appl. No.: 10/515,877

(22) PCT Filed: May 19, 2003

(86) PCT No.: PCT/EP03/05237

§ 371 (c)(1),
(2), (4) Date: Jun. 6, 2005

(87) PCT Pub. No.: WO03/102223

PCT Pub. Date: Dec. 11, 2003

(65) Prior Publication Data

US 2005/0255444 A1 Nov. 17, 2005

(30) Foreign Application Priority Data

May 31, 2002 (EP) .................................. 02405442

(51) Int. Cl.
*C12N 1/20* (2006.01)
*C12N 15/00* (2006.01)
(52) U.S. Cl. ................. 435/252.3; 435/320.1; 435/194; 536/23.2
(58) Field of Classification Search .............. 435/252.3, 435/320.1, 194; 536/23.2
See application file for complete search history.

(56) References Cited

OTHER PUBLICATIONS

Daunert et al. 2000.Genetically Engineered Whole-Cell Sensing Systems: Coupling Biological Recognition with Reporter Genes Chem, Review, vol. 100, p. 2705-2738.*
Mejare et al. 2001. Metal-binding proteins and peptides in bioremediation and phytoremediation of heavy metals, Trends in Biotechnology, 19, pp. 67-73.*
Cervantes et al., "Resistance to Arsenic Compounds in Microorganisms," FEMS Microbiology Reviews, 15, pp. 355-367, (1994).
Kaur et al., "Plasmid-Encoded Resistance to Arsenic and Antimony,", Plasmid 27, pp. 29-40 (1992).
Miller, et al., "Improved gfp and inaZBroad-Host-Range Promoter-Probe Vectors," MPMI, vol. 13. No. 11, pp. 1243-1250, (2000).
Scott et al., "Genetically Engineered Bacteria: Electrochemical Sensing Systems for Antimonite and Arsenite," Analytical Chemistry, vol. 69, No. 1, pp. 16-20, (1997).
Silver et al., "Pladmid-Mediated Heavy Metal Resistances," Ann. Rev. Microbiol, 42, pp. 717-743, (1988).
Sticher et al., "Development and Characterization of a Whole-Cell Bioluminescent Sensor for Bioavailable Middle-Chain Alkanes in Contaminated Groundwater Samples," Applied and Environmental Microbiology, pp. 4053-4060, (Oct. 1997).

Tauriainen et al., "Measurement of Firefly Luciferase Reporter Gene Activity from Cells and Lysates Using *Escherichia coli* Arsenite and Mercury Sensors," Analytical Biochemistry, 272, pp. 191-198, (1999).
Mejare et al., "Metal-Binding Proteins and Peptides in Bioremediation and Phytoremediation of Heavy Metals," Trends in Biotechnology, vol. 19, No. 2, pp. 67-73, (Feb. 2001).
Hug et al., "Arsenic Contamination of Ground Water: Disastrous Consequences in Bangladesh," EAWAG News 48, pp. 18-20, (English-language Abstract attached), (2000).
Ramanathan et al., entitled "Sensing Antimonite and Arsenite at the Subattomole Level with Genetically Engineered Bioluminescent Bacteria", Analytica Chemistry, American Chemical Society, vol. 69, No. 16, Aug. 15, 1997, pp. 3380-3384.
Ramanathan et al., entitled "Bacteria-Based Chemiluminescence Sensing System Using Beta-Galactosi-dase Under the Control of the ArsR Regulatory Protein of the Ars Operon", Analytica Chimica Acta, vol. 369, (1998), pp. 189-195.
Tauriainen et al., entitled "Recombinant Luminescent Bacteria for Measuring Bioavailable Arsenite and Antimonite", Applied and Enviromental Microbiology, vol. 63, No. 11, Nov. 1997, pp. 4456-4461.
Andersen, J.B. et al., entitled "New Unstable Variants of Green Fluorescent Protein for Studies of Transient Gene Expression in Bacteria", Appl. Environ. Microbiol. vol. 64, No. 6, Jun. 1998, pp. 2240-2246.
Cai J. et al., entitled "A Chromosomal Ars Operon Homologue of *Pseudomonas aeruginosa* Confers Increased Resistance to Arsenic and Antimony in *Escherichia coli*", Microbiology, vol. 144, (1998), pp. 2705-2713.
Carlin A. et al., entitled "The Ars Operon of *Escherichia coli* Confers Arsenical and Antimonial Resistance", J. Bacteriology, vol. 177, No. 4, Feb. 1995, 981-986.
Chen Y. et al., entitled "Metalloregulatory Properties of the ArsD Repressor", J. Biol. Chem., vol. 272, No. 22, May 30, 1997, pp. 14257-14262.
Daunert S. et al., entitled "Genetically Engineered Whole-Cell Sensing Systems: Coupling Biological Recognition with Reporter Genes", American Chemical Society, vol. 100, No. 7, Feb. 29, 2000, pp. 2705-2738.
"Arsenic Crisis Information Centre", Website:—http://www.bicn.com/acic/, pp. 1-4.
Jaspers M.C.M. et al., entitled "HbpR, a New Member of the XylR/DmpR Subclass within the NtrC Family of Bacterial Transcriptional Activators, Regulates Expression of 2-Hydroxybiphenyl Metabolism in *Pseudomonas azelaica* HBP1", J. Bacteriol., vol. 182, No. 2, Jan. 2000, pp. 405-417.

(Continued)

*Primary Examiner*—Tekchand Saidha
(74) *Attorney, Agent, or Firm*—The Webb Law Firm (57) ABSTRACT

The invention is concerned with a biologically based test system for the detection of inorganic and organic pollutants in water samples. In particular, the present invention is concerned with the development of a strategy for the control of background expression of biosensors in the biologically based test system. Furthermore, the present invention provides a test kit for determining concentrations of inorganic and organic pollutants in water samples, the test kits are suitable for field tests.

16 Claims, 6 Drawing Sheets

OTHER PUBLICATIONS

Kuroda M. et al., entitled "Alternate Energy Coupling of ArsB, the Membrane Subunit of the Ars Anion-Translocating ATPase", J. Biol. Chem., vol. 272, No. 1, Jan. 3, 1997, pp. 326-331.

Lang E. et al., entitled "Maintenance of Biodegradation Capacities of Aerobic Bacterial During Long-Term Preservation", Biodegradation, vol. 7, (1996), pp. 65-71.

Malik K.A., entitled "A New Freeze-Drying Method for the Preservation of Nitrogen-Fixing and Other Fragile Bacteria", Journal of Microbiological Methods, vol. 8 (1988), pp. 259-271.

Malik K.A. et al., entitled "Preservation of Immobilized Bacterial Cell-Matrix by Drying for Direct Use in Microbial Sensors", World Journal of Microbiology and Biotechnology, vol. 9, (1993), pp. 243-247.

McArthur J.M. et al., entitled "Arsenic in Groundwater:Testing Pollution Mechanisms for Sedimentary Aquifers in Bangladesh", Water Resources Research, vol. 37, No. 1, Jan. 2001, pp. 109-117.

* cited by examiner

BIOLOGICALLY BASED TEST SYSTEM

BACKGROUND OF THE INVENTION

The present invention relates to a biologically based test system for the detection of inorganic and organic pollutants in water samples. In particular, the present invention is concerned with the development of a strategy for the control of background expression of biosensors in said biologically based test system. More particularly, the present invention comprises a biologically based test system for the detection of arsenite and arsenate in potable water with a controlled background expression of the biosensor. Furthermore, the present invention provides a test kit for determining arsenite and arsenate concentrations in water samples, said test kits are suitable for field tests.

Arsenite and arsenate are found in toxic concentrations in groundwaters in many countries all over the world and seriously threaten the life of millions of people, especially in Southeast Asian countries, like Bangladesh. In the early 1990s, high levels of arsenic in potable water of Bangladesh were first detected. Presently, about 20 million people of the total population of Bangladesh (125 million) are suspected to be drinking contaminated water. Up to a certain degree, arsenic toxicity is reversible by drinking arsenic-free water. In Bangladesh, however, arsenic-free water is not available in many places and chronic poisoning develops. The effects of arsenic poisoning can vary from skin pigmentation, development of warts, diarrhea and ulcers during the initial stages. In the most severe cases, arsenic poisoning causes liver and renal deficiencies or cancer that can lead to death (6). It is assumed that the structural similarity with phosphate causes the toxicity of arsenate. Since arsenate mimics phosphate, it can be taken up through phosphate channels and can interfere in different metabolic processes (5), (9). Arsenic poisoning is undetectable in its early stages, and takes between 8 and 14 years to have a clear impact on human health. The final impact is depending on the amount of arsenic ingested, the nutritional status and the immune response of the individual.

More than ten years ago, most of Bangladesh's population obtained its potable water from surface ponds, but this was bacteriologically unsafe and, therefore, an undesired situation. Because of these reasons, the use of groundwater as source for potable water was promoted. It is estimated that 95% or more of Bangladeshis now use groundwater for drinking water. Unfortunately, the use of groundwater for drinking water has caused unsuspected dreadful effects, due to very high concentrations of arsenic. The content of arsenic in Bangladesh' groundwater is naturally determined.

The drinking water limit for As-contamination in Bangladesh is 50 µg/l. The World Health Organization, however, recommends an index of 10 µg/l. The highest concentrations of arsenic found in Bangladesh are around 2.4 mg/l. Arsenic in potable water is not only a problem in Bangladesh, but also in other countries like India, Mexico, Vietnam or the Republic of Yugoslavia. Measuring the concentrations of arsenite and arsenate in water used as drinking water is therefore an absolute necessity. Accurate determination of arsenic compounds is usually done by Atomic Fluorescence Spectroscopy or Atomic Adsorption Spectroscopy, but both techniques require substantial investments and are not available in rural and poorer areas. Chemical field tests exist as well, but these are not accurate in the range of the present drinking water standards (10 to 50 microgram per liter) and themselves give rise to pollution with heavy metals like mercury and zinc. Moreover, the measurement of arsenite by traditional analytical chemical methods is difficult and costly (23). Thus, there is a strong interest to produce chemical field test kits, which are sensitive enough to detect arsenite around the drinking water limit of 50 µg/l. Most available tests use hydrochloric acid and zinc to produce arsine-gas ($AsH_3$), which is then reacting with mercuric bromide on a paper, producing a brown color. However, this test is still unreliable at concentrations below 150 µg/l.

Alternative measuring strategies could involve an assay with whole cell living biosensors. Such assays have already been described in the art. In this type of biosensor assay microorganisms are used as specific and sensitive devices for sensing the bioavailability of a particular pollutant or pollutant class (21). The idea of sensing is based on the ability of pollutants to invoke a specific and inducible response in microorganisms. The signaling pathway thus activated will regulate the expression of one or more genes. The extent of this gene expression serves as a measure of the available ("sensed") concentration of the compound. A rapid and sensitive way to measure such gene expression is to fuse relevant promoter sequences to reporter genes, like those coding for bacterial luciferase, beta-galactosidase or green flurorescent protein (GFP).

A bacterial bioassay has been described (16, 17, 19, 22 and 23), which is based on the natural resistance mechanisms of bacteria against arsenic. This assay makes use of biosensors, which are able to detect arsenite and arsenate in water samples. Said biosensors are usually genetically modified bacteria, comprising a gene coding for a regulatory protein inducing the production of a specific marker protein in the presence of arsenic. The biosensors are remarkable sensitive and detect arsenite at concentrations of 5 microgram per liter. The activity of the marker protein is usually measured by a luminometer.

However, bioassays developed so far are afflicted with high background expressions of the marker proteins, which lead to false positive results at arsenite concentrations in the microgram per liter range and this has limited until now the development of a simple field colorimetric test. Background expression occurs in all arsenic-based biosensors due to the nature of the DNA-binding of the regulatory protein.

Therefore, an urgent need exists for the development and availability of a simple, cheap, reliable, and accurate test system with a controlled background expression of the biosensor, which is suitable as a field test for the measurement of heavy metals, such as arsenic in water samples.

SUMMARY OF THE INVENTION

The present invention solves the above-mentioned problem by providing an improved biologically based test system for the detection of pollutants in water samples comprising a genetically modified bacterium producing a marker protein upon induction of a regulatory protein, wherein the activity of said regulatory protein is induced by the presence of said pollutant, characterized in that said genetically modified bacterium comprises at least one additional DNA binding site for the regulatory protein directly in front of the gene for the marker protein.

More particularly, the present invention provides an improved test system for the detection of heavy metals such as arsenite and arsenate in water samples.

DETAILED DESCRIPTION OF THE INVENTION

Many bacterial strains, like *Ralstonia metallidurens, Pseudomonas aeruginosa* or *Staphylococcus aureus* contain genetic determinants for resistance to heavy metals such as $Hg^{2+}$, $Ag^{2+}$, $AsO_2^-$, $AsO_4^{3-}$, $Bi^{3+}$, $BO_3^{3-}$, $Cd^{2+}$, $Co^{2+}$, $CrO_4^{2-}$, $Cu^{2+}$, $Ni^{2+}$, $Pb^{3+}$, $Sb^{2+}$, $TeO_3^{2-}$, $Tl^+$, or $Zn^{2+}$ (20). These resistance determinants are often found on plasmids and/or transposons. Resistance to arsenic and antimony are also associated with plasmid-encoded resistance operons, which are widespread among bacterial species, although many bacteria carry arsenite resistance genes on the chromosome. Bacterial resistance to arsenite (As(III)), arsenate (AS(V)) and antimonite (Sb(III)) is found both in gram-negative and gram-positive bacteria (3).

Thus, in a preferred embodiment of the present invention the genetically modified bacteria is an *Escherichia coli* strain bearing a genetically modified plasmid; said plasmid carrying an arsenite resistance regulatory gene, a gene coding for a marker protein and at least one additional DNA binding site for an arsenite resistance regulatory protein in front of the gene for the marker protein in order to reduce background expression.

In yet another preferred embodiment the *Escherichia coli* strain is the strain *E. coli* K12, the arsenite resistance regulatory gene is derived from the naturally occurring *E. coli* plasmid R773, cloned into any suitable *E. coli* K12 plasmids like pBR322, pUC18, pACYC184 and RSF1010.

As already mentioned the present invention uses the naturally occurring plasmid R773 of *Escherichia coli* as source for the arsenite resistance gene. The specific DNA region of this plasmid conferring arsenic and antimony resistance is known as the ars operon. The system demonstrates a high selectivity for arsenite and antimonite, and, to a lesser extent to bismuth oxide. Other anions like phosphate, carbonate, nitrate and sulfate do not induce the system (19).

The ars operon of *E. coli* plasmid R773 contains five genes, encoding the proteins ArsR, ArsD, ArsA, ArsB and ArsC. ArsR and ArsD are so-called regulatory proteins. ArsR controls the basal level of protein expression, whereas ArsD controls the maximal level of protein expression. ArsA and ArsB form a pump to remove antimonite and arsenite from the cytosol to the periplasm of the bacteria. ArsA is an ATPase that provides the energy necessary for this process and ArsB is the transmembrane protein. ArsC reduces arsenate to arsenite, which can then subsequently be effluxed by the pump (17).

Figure 1:
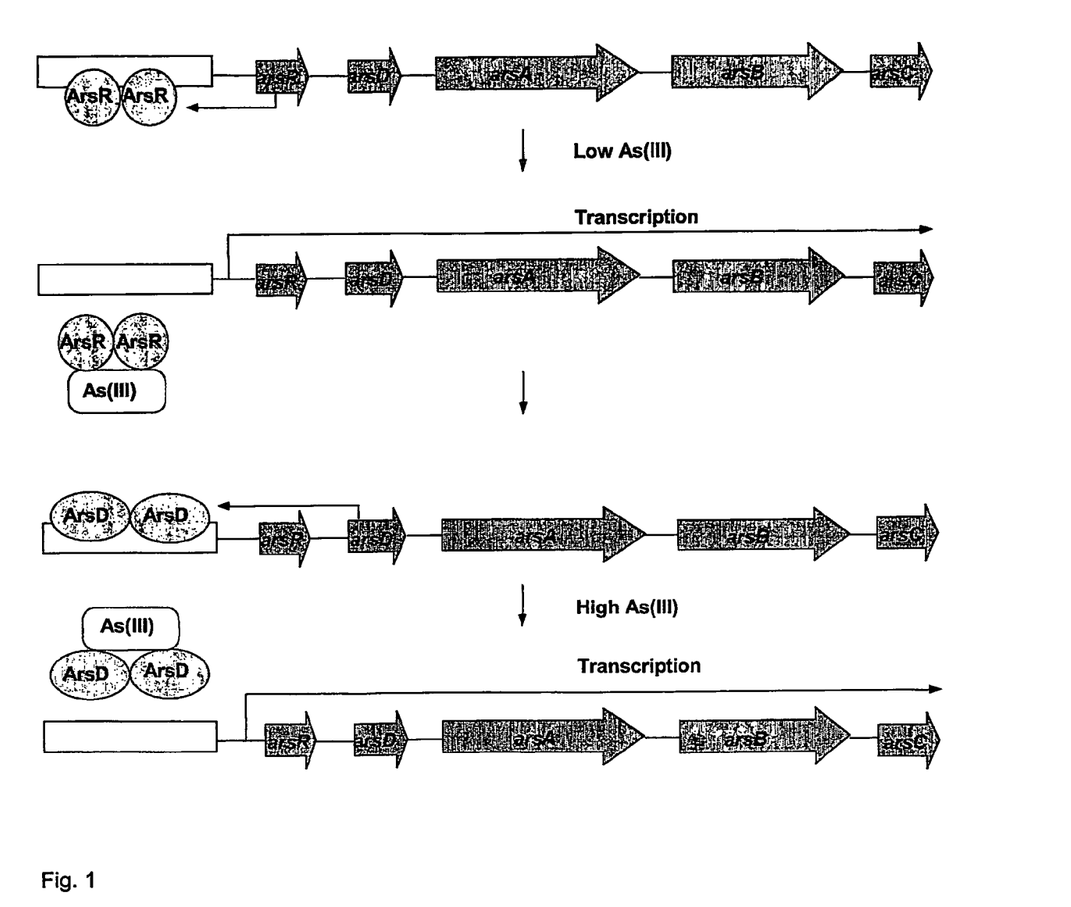
FIG. 1 is a scheme of the regulation and organization of the ars genes.
Figure 2:
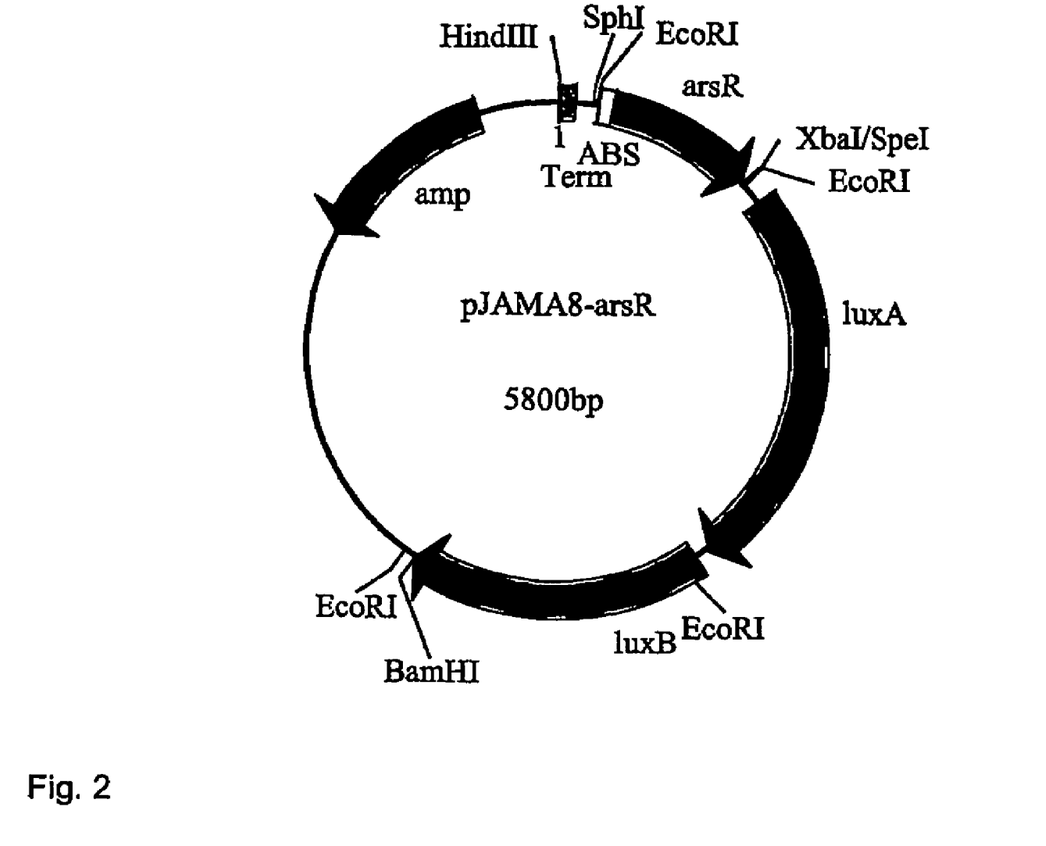
FIG. 2 shows a schematic drawing of plasmid pJAMA8-arsR. In front of the arsR-gene is a terminator structure ('Term'), followed by the arsR-promoter and binding site for ArsR ('ABS'). Located behind the arsR-gene are the genes for bacterial luciferase ('luxA' and 'luxB'). Positions of relevant restriction sites are indicated.
Figure 3:
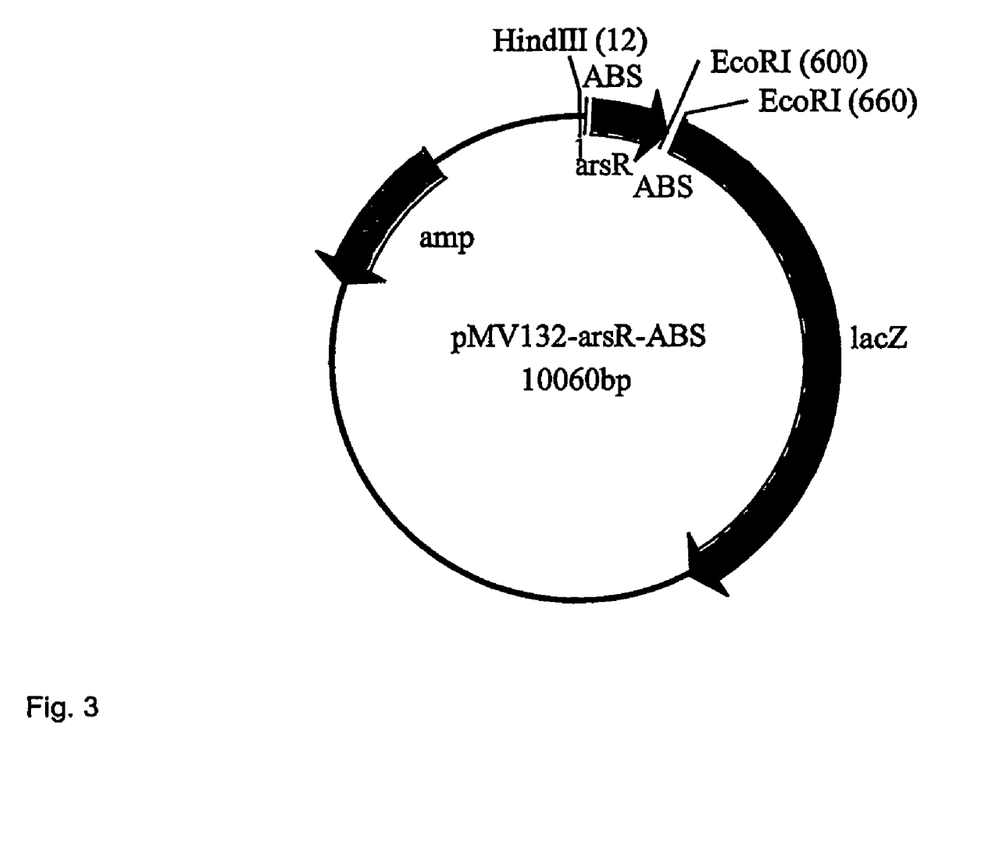
FIG. 3 is a schematic drawing of the plasmid used for colorimetric detection of arsenite contamination. Abbreviations and symbols as in FIG. 2.

The signaling pathway for arsenic sensing functions as follows: In the absence of antimonite or arsenite the ArsR protein binds to the DNA near the promoter region of the ars operon, repressing transcription of the ars genes. When arsenite or antimonite enter the cell, they bind to ArsR and cause a conformational change in the protein, which results in the release of ArsR from the promoter DNA. Transcription of the ars operon then starts. Arsenate (AsV) itself does not directly induce ars transcription. When the intracellular concentration of ArsD becomes sufficient to saturate the operator, transcription is again repressed. At higher As(III) or Sb(III) concentrations, ArsD dissociates from the operator, producing again an increase in ars expression (4), (2), (see FIG. 1). Regulation of the ars operon is mediated from a site on the DNA in front of the arsR gene, to which the ArsR protein binds. The natural system is expressed constitutively to a low level, without which ArsR itself would not be synthesized and the cycle of repression and repression-release would not function.

For purposes of the present invention only the gene coding for the ArsR protein was isolated from the plasmid R733 and transcriptionally fused to a gene coding for a marker protein downstream of arsR. Upon activation of the ars operon the marker gene fusion is transcribed. However, due to the said nature of the ArsR activation cycle, a low transcription of the gene for the marker protein will occur in absence of arsenite.

In the present invention the low constitutive transcription of the marker gene is effectively reduced by placing another binding site for ArsR downstream of the gene for arsR and in front of the marker gene.

In a further embodiment of the present invention the gene coding for a marker protein is selected from the group comprising alkaline phosphatase (phoA), chloramphenicol acetyl transferase (CAT-gene), catechol dioxygenase (xylE), bacterial luciferase, eukaryotic luciferase, beta-galactosidase, and green fluorescent protein (GFP), most preferably bacterial luciferase, green fluorescent protein and beta-galactosidase.

Genes coding for such marker proteins are widely used as so called reporter genes. They are linked to other genes or regulatory sequences, in the present invention to the arsR gene of the ars operon of plasmid R773 or any other arsR gene, in order to indicate their activity.

Another very important embodiment of the present invention comprises a biologically based test kit for the determination of heavy metal in water samples, said test kit is suitable for field tests in that it can be stored at room temperature and is easily decontaminated.

In a preferred embodiment the biologically based test kit of the present invention comprises a colorimetric paper strip comprising genetically modified bacteria, said bacteria containing a plasmid conferring resistance to a heavy metal and being immobilized and dried in a matrix on the calorimetric paper strip.

In yet another preferred embodiment of the present invention the test kit is suitable for the detection of arsenite and arsenate in water samples.

In a more preferred embodiment the genetically modified bacteria immobilized on the paper strip are derived from the *E. coli* strain K12, the arsR gene is derived form the naturally occurring plasmid R773 and introduced into a suitable *E. coli* plasmid vector, said plasmid vector being genetically modified by carrying at least one additional DNA binding site for the ArS protein.

Another embodiment of the present invention is a method for preparing a calorimetric paper strip test kit, comprising the steps of:
a) Cultivating bacterial cells;
b) Transferring 5 to 20 microliter, preferably 10 microliter of the bacterial suspension of step a) on small paper strips;
c) Placing the paper strips in sterile tubes; and
d) Drying of the paper strips under constant temperatur and gradually lowered vacuum.

A further embodiment of the present invention comprises a biologically based test kit for the determination of heavy metal concentrations, such as arsenite and arsenate concentrations in water samples, said test kit comprising a multi-well plate coated with genetically modified bacteria derived from the *E. coli* strain K12, said bacteria comprising an *E. coli* plasmid vector carrying the gene coding for the arsenite resistance protein ArsR from the naturally occurring plasmid R773, said plasmid vector carrying at least one additional DNA binding site for the ArsR protein.

A further embodiment of the invention is a method for producing a multi-well test kit, comprising the steps of:
a) cultivating bacterial cells;
b) transferring 30 to 70 microliter, preferably 50 microliter of the bacterial suspension of step a) into a glass vial or multi-well plate; and
c) drying of the bacterial suspension under constant temperature and gradually lowered vacuum.

Another preferred embodiment of the present invention is the use of the described test kits in field tests for the detection of arsenite and arsenate in water samples.

The following examples are intended to further illustrate the present invention. They are meant to be exemplary to the invention and do not to limit its scope.

EXAMPLES

Two types of whole cell living biosensors are described. Both consist of the bacterium Escherichia coli K12, a non-pathogenic laboratory strain, into which different plasmids—with the sensing elements—are introduced. One of these produces the luciferase enzyme upon contact of the bacteria with arsenite. The activity of the luciferase enzyme results in light production and can be measured very sensitively and quantitatively. The second biosensor produces the enzyme beta-galactosidase upon contact of the bacteria with arsenite. The activity of beta-galactosidase can be assayed by the formation of a colored compound. This second biosensor formed the basis for a quick semi-quantitative field color test.

Example 1

Construction of a Biosensor for Arsenic Detection Based on Luciferase

Figure 4:
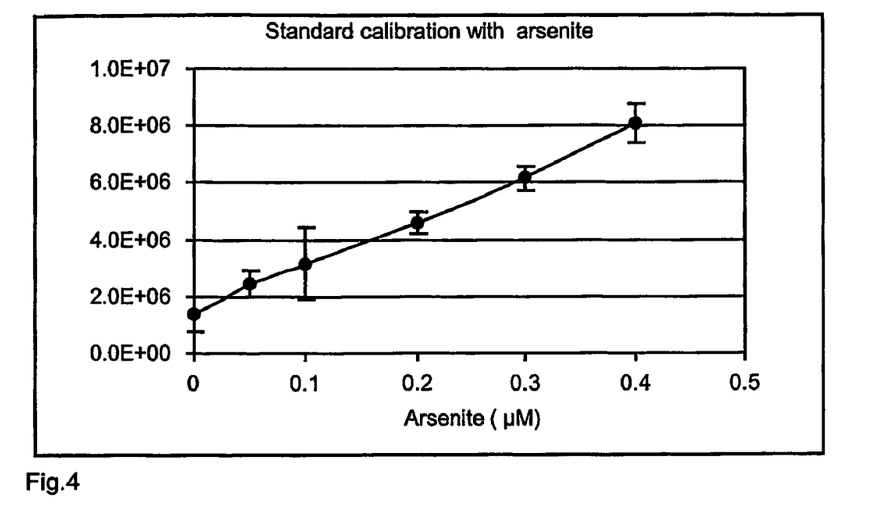
FIG. 4 demonstrates light emission from the biosensor cells (E. coli DH5α pJAMA8-arsR) in response to different arsenite concentrations after 30 minutes exposure time. Shown are the averages of three independent incubations mixed from three frozen batches of biosensor cells. Vertical bars indicate the calculated deviation from the average (assuming normal distribution). Multiwell assay with a total volume of 0.2 ml and 0.05 ml cell culture.

For reasons of detection accuracy and ease of the measurement, a biosensor in E. coli was produced, which would produce light (=bioluminescence) in response to the presence of arsenite. By genetic engineering techniques known in the art, a DNA fragment containing the promoter for arsR (ParsR) and the gene for arsR was isolated, which was in vitro combined with a DNA fragment containing the genes for bacterial luciferase (luxAB). This plasmid, pJAMA8-arsR, was then reintroduced into E. coli strain DH5α (FIG. 4). E. coli DH5α is a laboratory strain and derivative of E. coli K12, classified to the lowest biosafety level and without any known pathogenicity determinants. The response of this E. coli (pJAMA8-arsR) was carefully calibrated and found to be sufficient to detect arsenite in the range below 0.1 μM arsenite (8 μg/l).

Example 2

Beta-Galactosidase Based Detection

The main purpose of producing a whole cell living biosensor for arsenite with the gene for beta-galactosidase as detection system was the potential for a color test kit. The activity of the beta-galactosidase enzyme can be measured in various ways. The easiest one involves the addition of a colorless substrate (X-Gal), which is turned into a blue dye by cleavage with active beta-galactosidase. X-Gal is directly taken up by the bacteria and there is no need to permeabilize or open the cells.

The original plasmid pBGD23 did not allow the use of X-Gal as a substrate, since the background beta-galactosidase activity in the bacteria was too high. This means that even without any arsenite present, some beta-galactosidase is synthesized in the cells, which cleaves X-Gal and produces the blue color. The reason for this background activity lays in the nature of the ArsR regulatory system. Thus, a plasmid was produced in which the background activity from the lacZ gene is very low. This was achieved by adding a small DNA fragment containing the binding site for the ArsR protein, in between the end of arsR and the beginning of lacZ. In this way, most of the transcription was blocked after the arsR gene.

This new plasmid was constructed in several steps. First, a fragment containing ParsR and arsR was isolated and cloned in front of a promoterless lacZ gene (plasmid pMV132). This plasmid was then opened at a unique restriction site in front of lacZ and a 60-base-pair small DNA piece was inserted which carried the binding site for ArsR. The resulting plasmid was named pMV132-arsR-ABS. E. coli cells carrying this plasmid could indeed be used to produce a color gradient of blue at concentrations as low as 0.1 μM in a response time of 1 hour, both in multi-well plate format and on paper strips.

Example 3

Measuring with Arsenic Biosensors

In a first instance, both biosensor variants were tested for their capability to detect arsenite in the environmentally relevant concentration range (0-0.5 mg/l), to test the influence of incubation time on the test result, to determine the reproducibility of the biosensor measurement and the influence of disturbing compounds in the water samples. The arsenite concentration in unknown aqueous samples can be inferred by comparing the light signal to that of a standard curve produced with known arsenite concentrations. Inhibitory effects of other chemical compounds present in the sample can be addressed by addition of a known amount of arsenite to the sample and comparing the observed increase in light emission with the light emission expected from the calibration curve.

Example 4

Calibration Series with Arsenite

Calibration series with arsenite were performed with a stock solution of 1 g/l arsenite, which was diluted in water until the desired concentration range (0.1 to 1 µM—with 1 µM corresponding to 78 µg/l). At first, optimal conditions for the biosensor measurements were used. This involved the use of cell batches, which were frozen at −80° C. and thawed before each measurement. The cells from one frozen batch (0.6 ml) could be divided in 4 portions, in order to perform a complete calibration series with one batch of cells. In some cases, batch-to-batch variations were noticed and, therefore, a protocol of deriving three cell batches was used, thawing and mixing those, and preparing from these three parallel calibration series. Initially, tests were performed in individual glass tubes for each measurement. However, for more convenient and faster measurements, the procedure was changed to using 24-well or 96-well plates.

Figure 5:
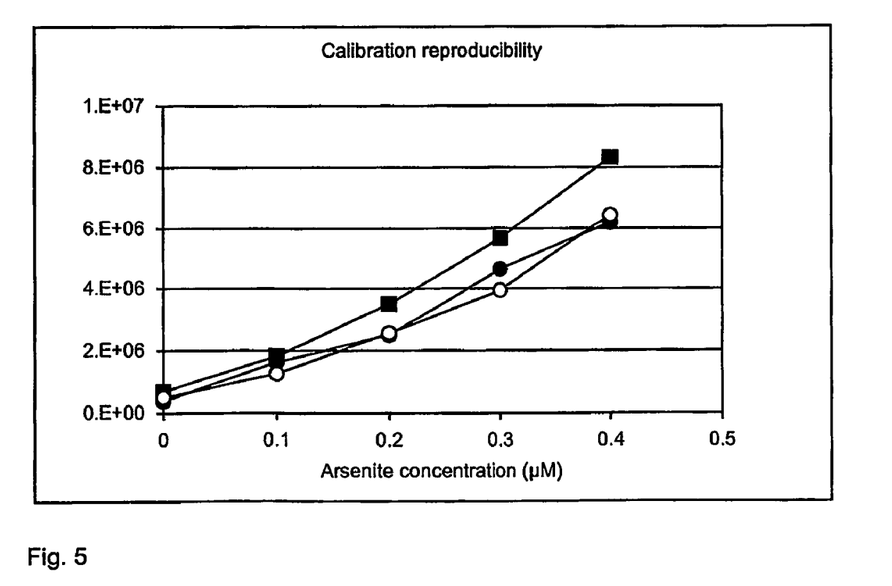
FIG. 5 shows the reproducibility of biosensor calibration in response to different arsenite concentrations. Calibration curves were produced by three different individuals from different frozen cell batches on the same day. Induction time: 30 minutes. Data points in each curve indicate the averages from two independent incubations from the same batch.

As can be seen from a typical calibration curve as shown in FIG. 4 the light emission from the cells recorded after 30 minutes incubation time, increases proportionally to the arsenite concentration in the medium. Some background light emission occurs even without arsenite present. The reason for this was the background expression from the ParsR—since the luciferase sensor plasmid was not corrected for its background expression like the beta-galactosidase sensor plasmid. However, the background expression did not interfere with the measurements in the lower range (i.e., below 0.1 µM arsenite). Addition of the second ArsR binding site to the same plasmid resulted in reduction of the background expression (not shown). The absolute light emission from the cells increased when the incubation time with arsenite was prolonged. Therefore, the absolute light emission value should not be taken as an indication for the arsenite concentration, but only in combination with a calibration curve performed simultaneously. Despite this, the reproducibility of the calibration curve prepared from frozen cell batches by different individuals within the same laboratory was good (FIG. 5).

The arsenic biosensor expressing the beta-galactosidase was used in a similar way as the luciferase sensor. In such a quantitative test, the activity of beta-galactosidase was analyzed by permeabilizing the sensor cells, adding the substrate for the enzyme (ONPG) and recording the increase in absorption at 420 nm. It was also addressed, however, if the beta-galactosidase induced in $E.$ $coli$ strain containing plasmid pMV132-arsR-ABS could be analyzed by the formation of a colored product. In this way, different intensities of blue color were produced which were dependent on the arsenic concentration measured by the cells. However, no absolute assignment could be made to the intensity of the blue color, since this increases during longer incubation times. However, the intensity increase was not a matter of minutes, but rather of half-an-hour or longer, and the differences among incubations with different arsenite concentrations remained similar for incubation periods as long as 12- to 16 hours. Therefore, this sensor can be used to have a quick first screening of samples. The lower detection limit was around 0.1 µM arsenite.

Example 5

Calibration Series with Arsenate

Since arsenite is only one of the various forms in which arsenic contamination can occur, calibration series with arsenate were performed. From previous work it was known that the biosensor strain might also react to arsenate, since many $E.$ $coli$ host strains carry the arsenate reductase enzyme. This enzyme reduces arsenate to arsenite within the cell and the produced arsenite triggers the induction of the gene reporter construct.

Figure 6:
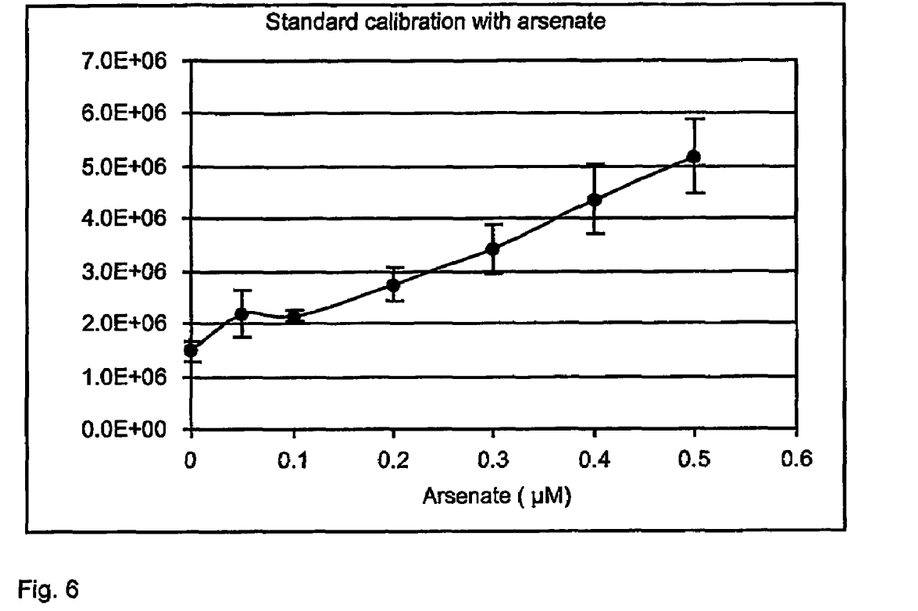
FIG. 6 demonstrates standard calibration of E. coli DH5α (pJAMA-arsR) with arsenate. Data points are the averages of three independent incubations mixed from four frozen cell batches. Incubation time: 30 minutes. Incubation temperature: 37° C. Multiwell assay with 1 ml total volume and 0.15 ml cell culture.

Indeed, in the host strain $E.$ $coli$ DH5α, the plasmid pJAMA-arsR resulted in the production of luciferase upon incubation with arsenate. The response was about half as strong as that with arsenite (FIG. 6). The small 'hill' in the calibration curve around 0.1 µM was not consistently observed and, therefore, likely is the result of a measurement outlayer. From these measurements it was concluded that the sensor is also sensitive enough to measure arsenate in the range below 0.2 µM.

The biosensor strain with the beta-galactosidase reacted similarly to arsenate as to arsenite (not shown).

Example 6

Disturbances and Cross-Reactivity

Since the biosensor measurements were performed with whole cells of living bacteria, several factors other than the target compound could influence the output (the 'measurement') of the sensor cells. Of most important concern are those compounds present in the water sample, which are toxic for the bacterial cells or otherwise interfering with the chemical status of arsenic. It is not possible to test each possible combination of compounds on the behaviour of the biosensor cells. Therefore, we focused on the effects of iron—which is a major constituent of groundwater and known to chemically interfere with arsenic, and further compared biosensor and chemical arsenic measurements in a number of imported Bangladesh groundwater samples.

Figure 7:
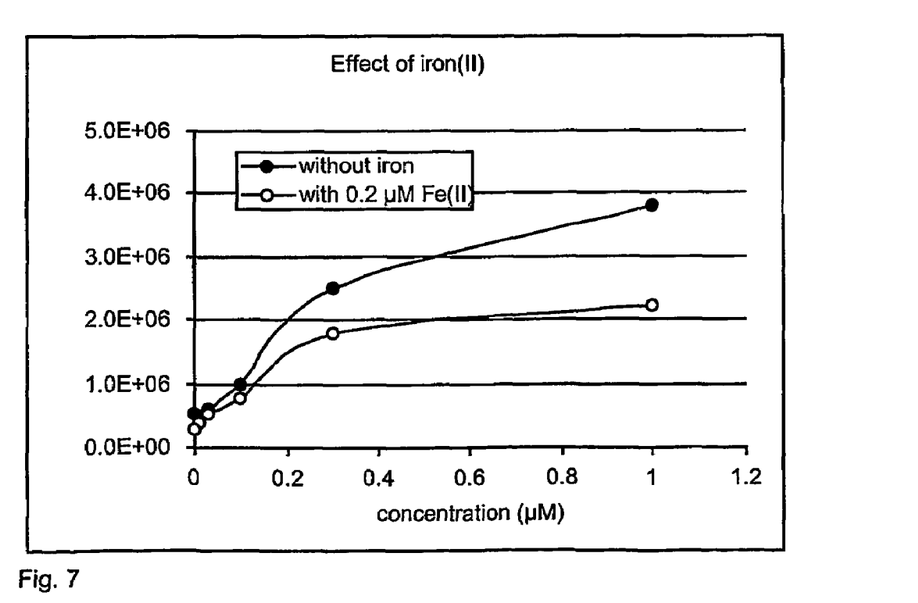
FIG. 7 shows the effect of 0.2 μM FeSO4 on the light emission of the biosensor exposed to a range of arsenite concentrations. Incubation time: 30 minutes at 37° C. Data points indicate the average from two independent assays.
Figure 8:
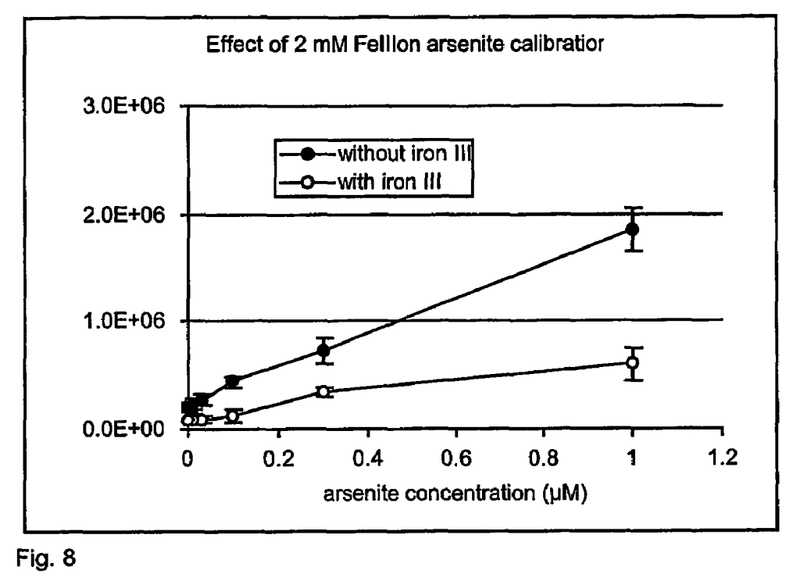
FIG. 8 shows the effect of 2 mM Fe$_3$EDTA on the light emission of the biosensor exposed to a range of arsenite concentrations. Incubation time: 30 minutes at 37° C. Data points indicate the average from three independent assays. Vertical bars point to the average deviation.
Figure 9:
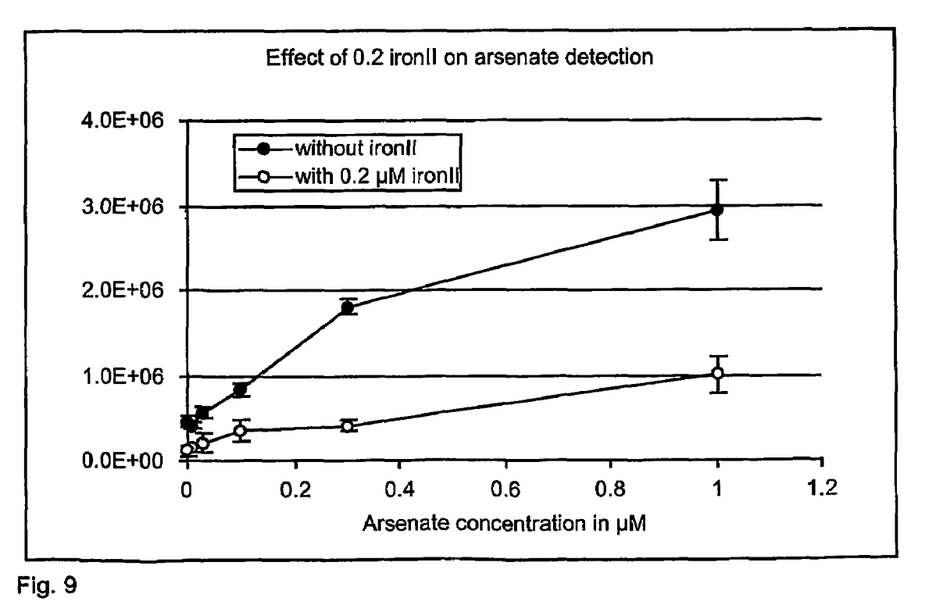
FIG. 9 shows the effect of including 0.2 μM FeSO4 on the light emission of the biosensor exposed to a range of arsenate concentrations. Incubation: 30 minutes at 37° C. Data points indicate the average from three independent assays. Vertical bars point to the average deviation.

As far as biosensor measurements showed, mostly iron II reduced the output from the sensors (FIGS. 7-9). Iron II was tested in a concentration of 0.2 µM (=11 mg/L) and this resulted in about 50% reduction of light emission at the highest arsenite concentration tested. At lower arsenite concentrations, the effect was not so pronounced (FIG. 7). It was suspected that the effect of iron II might have been a complexation with arsenite, thereby reducing the available arsenite fraction, although also samples without arsenite showed a reduced light emission in the presence of 0.2 µM iron (II) (FIG. 9).

Cross-reactivity of the arsenite sensor was only observed to antimonite and bismuth. The inductive response to antimonite is as sensitive as that to arsenite (not shown), whereas that to bismuth oxide is 100-fold less sensitive. Therefore, in theory, antimonite and arsenite could interfere and positive measurements may lead to false interpretations when under no other circumstances a confirmation is made by using atomic adsorption spectrometry.

Example 7

Analysis of Groundwater Samples from Bangladesh and Vietnam

Several groundwater samples, which had been taken in Bangladesh, were analyzed by using the luciferase and beta-galactosidase biosensors. Since the water samples had been acidified for storage and transport, they were diluted 10- and 100-fold in phosphate buffer of pH 7. To test for any inhibitory compounds in the water for the biosensor cells, one extra measurement was performed in which the samples were spiked with an additional 0.2 μM arsenite. When no inhibitory factors would be present, the light emission would increase according to the calibration curve (except if the arsenite concentration in the sample would be higher than 1 μM).

As can be seen from the results, all samples except B4 contained arsenic in amounts higher than the 10 μg/L limit, except sample B4 (Table 1). The results from the spiked samples indicate that except for the highest value (B1), no inhibitory compounds were present for the biosensor. The water of well B1 is in the range of the maximal response of the biosensor. Therefore, any increase of arsenite concentration will result in a lower light emission, since arsenite starts to become toxic for the cells. For water samples B1, B2 and B3, the total concentration of arsenic by chemical analyses was more ore less in agreement with the concentration determined by the biosensor (B1: 1020 compared to 980, B2: 375 compared to 210, B3: 407 compared to 224). Samples B4 and B7 were clearly higher in the chemical analysis (256 and 265 μg/L, respectively). The reasons for this difference are presently not clear yet.

In the colorimetric test (FIG. 10), tenfold dilutions of the same samples B1, B2, B3, B4 and B7 scored positive at a concentration range between 0.1 and 0.5 μM As (=8 and 50 μg/L). This is in agreement with the chemical analyses, except for sample B1, which is even higher than 0.5 mg/L.

Example 8

Development of a Storage Protocol

One of the critical factors for the use of the biosensor test is its storage. Sufficiently well-equipped laboratories can use the most easy variant of freezing cell batches in 15% glycerol at −80° C. and thawing these before use. Preserved in this manner, the cell batches keep viable and active for at least 1 year. Less well-equipped laboratories can grow the biosensor cells fresh for each measurement and maintain optimal results. In order to provide a possibility to perform the arsenic biosensor test without worrying about preservation or cultivating the bacterial cultures, a storage protocol was developed. The storage protocol was based on studies by Dr. K. Malik from the German Collection of Microorganisms. By using his protocols it was possible to produce dried biosensor cultures, which retained their activity for arsenic measurements during one month storage at room temperature. This may be improved with more optimal storage conditions and optimized drying materials.

Example 9

Protocol for Liquid Drying

The protocol for liquid drying consists of three steps: cultivating the bacterial cells, drying and storage, and testing.
i) bacterial cultures were grown from a fresh colony in 5 ml liquid medium (Luria Broth) containing ampicillin for 16 h at 37° C. Cells were then harvested by centrifugation and the supernatant removed. The cell pellet was carefully resuspended in a medium containing gelatin, meat extract, sodium ascorbate, raffinose and sodium glutamate. Drops of 50 microliter of culture suspension were transferred to 2 ml glass vials, which were closed with a screw-cap and Teflon seal. The Teflon seal was punctured with a small-gauge needle.

TABLE 1

Determination of arsenite-equivalent concentrations in Bangladesh' groundwater samples.

| Sample nr | Light emission Meas 1 | Meas 2 | Average | Arsenic concentration according to AsIII standard curve As (μM) | Correction for dilution and inhibition As corr | Arsenic concentration As (μg/L) |
|---|---|---|---|---|---|---|
| B1 | 10951380 | 13426902 | 12189141 | 0.66 | 13.2 | 980 |
| B2 | 3693575 | 3749482 | 3721529 | 0.14 | 2.8 | 210 |
| B3 | 3382199 | 4382695 | 3882447 | 0.15 | 3.0 | 224 |
| B4 | 1727514 | 1566010 | 1646762 | 0.01 | 1.22 | 17 |
| B7 | 2208496 | 1655100 | 1931798 | 0.03 | 0.56 | 44 |
| Spiked samples | | | | | Expected increase | |
| B1 | 7999680 | 10225318 | 9112499 | 0.47 | 0.86 | |
| B2 | 6169947 | 6548613 | 6359280 | 0.30 | 0.34 | |
| B3 | 8034159 | 7916240 | 7975200 | 0.40 | 0.35 | |
| B4 | 4819680 | 3999806 | 4409743 | 0.18 | 0.21 | |
| B7 | 6175502 | 5561221 | 5868362 | 0.27 | 0.23 | | ii) Drying was performed at a constant temperature of 20° C. and gradually lowered vacuum. First, 1 h was dried at 70 mbar, the next hour at 20 mbar, after which the samples were dried at 0.5 mbar for another 12 h. The vacuum chamber was then filled with nitrogen gas and the vials closed. For storage the caps of the vials were sealed with parafilm and the vials were maintained in the dark at room temperature (20-25° C.).

iii) Tests with dried cultures were performed as follows: the dried cells were reconstituted with 0.5 ml water for 20 minutes. Measurement was continued by incubating for 30 minutes, 1 h or 2 h at 37° C., after which light emission was recorded in a luminometer.

Example 10

Protocol for Paper Drying

The protocol for paper drying was similar to that of liquid drying.

i) bacterial cultures were grown from a fresh colony in 5 ml liquid medium (Luria Broth) containing ampicillin for 16 h at 37° C. Cells were then harvested by centrifugation and the supernatant removed. The cell pellet was carefully resuspended in a medium containing gelatin, meat extract, sodium ascorbate, raffinose and sodium glutamate. Drops of 10 microliter of culture suspension were pipetted on small Whatman 3M paper strips. Up to 6 strips were placed inside a 10 ml sterile tube.

ii) Drying was performed at a constant temperature of 20° C. and gradually lowered vacuum. First, 1 h was dried at 70 mbar, the next hour at 20 mbar, after which the samples were dried at 0.5 mbar for another 12 h. The vacuum chamber was then filled with nitrogen gas and the vials closed. For storage the tubes with were maintained in the dark at room temperature (20-25° C.).

iii) tests with the dried paper cultures were performed as follows. One paper strip was placed in a vial containing 1 ml of water sample and incubated for 30 minutes at a temperature between 30 and 37° C. After 30 minutes the strips were taken out from the vial and placed on a plastic surface. 1 drop of X-Gal substrate solution for the beta-galactosidase enzyme was added to the spot with bacterial cells. After incubating for 15 minutes or longer (depending on the desired intensity of the spots) the blue color development was judged in comparison to a standard series containing zero, 0.1, 0.2 and 0.5 µM arsenite.

Example 11

Survival and Activity Tests with Dried Biosensor Cultures

Dried cultures in glass vials were stored at room temperature for periods up to one month. At regular intervals bacterial pellets were resuspended in water and dilution series prepared, or suspensions used for testing the immediate induction with 0.4 µM arsenite (Table 3). Directly after drying, the viability of the cultures was around 30% compared to before drying, which decreased to about 10% after one week. In some cases, the viability dropped to 1% after 21 days, whereas for other batches viability retained approximately 10% after three weeks. The reasons for this difference are presently not clear.

The changes in viability were more or less reflected in the potential to become immediately activated by arsenite (Table 2). The total light emission by the cultures decreased upon prolonged storage times, although the difference (or induction factor) between blanc (no arsenite) and 0.4 µM was retained, even after 21 days storage. For most luminometers, there is no problem to measure even in the range of 1000 to 10000 relative light units.

Table 2. Light emission after three induction times of dried cultures stored at room temperature. Test concentrations: zero and 0.4 µM arsenite.

|  | 30 min | 1 h | 2 h | Induction factor(2 h) |
|---|---|---|---|---|
| 1d storage |  |  |  |  |
| 0.4 µM | 797691 | 2545974 | 7264655 | 2.9 |
| 0 | 547705 | 2085406 | 2487514 |  |
| 8d storage |  |  |  |  |
| 0.4 µM | 159678 | 615092 | 1973606 | 3.5 |
| 0 | 107123 | 230976 | 557872 |  |
| 21d storage |  |  |  |  |
| 0.4 µM | 714 | 7047 | 50622 | 7.2 |
| 0 | 310 | 1501 | 6966 |  |

Example 12

Decontamination

One of the concerns with using bacterial biosensors is that they are genetically modified bacteria. For the construction of the arsenic biosensor bacteria, the following precautions were made:

A poor-surviving well known laboratory strain of *E. coli* was used for cloning, which has a long history of usage all over the world without any known pathogenicity effects and Mostly isogenous characteristics were used: both arsR and lacZ originate from *E. coli* itself. The luciferase genes originate from *Vibrio harveyi* but do not have pathogenicity characteristics All plasmids used are non-mobilizable and only replicate in *E. coli*.

As selection marker resistance to the antibiotic ampicillin was used, which is not in clinical use and therefore is not considered to lead to increased acquired antibiotic resistance among pathogenic microorganisms.

Despite those measures, the question remained as to what should be done with the biosensor strains after their use for a measurement and how decontamination should take place. Considering used paper strip test, the best contamination is to burn them. With respect to liquid biosensor tests, most bacteria were quickly killed by acidifying the water-biosensor-sample with a few drops of lemon juice. This showed that almost immediately a 4-log reduction in viability could be achieved by lowering the pH. Further reduction can be achieved by more regular methods: i.e., exposure to sunlight and heat. In this respect, the used *E. coli* strains are poor survivors, which is also reflected by the difficult efforts to prepare and maintain activity in dried cultures.

REFERENCES

1. Andersen, J. B., Sternberg, C., Poulsen, L. K., Bjorn, S. P., Giskov, M., and Molin, S. 1998. New unstable variants of Green Fluorescent Protein for studies of transient gene expression in Bacteria. Appl. Environ. Microbiol. 64:2240-2246.

2. Cai J., S. K., and DuBow M. S. 1998. A chromosomal ars operon homologue of *Pseudomonas aeruginosa* confers increased resistance to arsenic and antimony in *Escherichia coli*. Microbiology. 144:2705-2713.

3. Carlin A., W. S., Dey S. and Rosen B. P. 1995. The ars operon of *Escherichia coli* confers arsenical and antimonial resistance. J. Bacteriol. 177:981-986.

{Number not correct!} 3: Cervantes C, Ji G, Ramirez J L, Silver S. Resistance to arsenic compounds in microorganisms. FEMS Microbiol Rev. 1994 December; 15(4):355-67.

4. Chen Y., Rosen B. P. 1997. Metalloregulatory properties of the ArsD Repressor. J. Biol. Chem. 272:14257-14262.

5. Daunert, S., Barrett, G., Feliciano, J. S., Shetty, R. S., Shrestha, S. and Smith-Spencer, W. 2000. Genetically engineered whole-cell sensing systems: coupling biological recognition with reporter genes. American Chemical Society 6. http://www.bicn.com/acic/

7. Hug, S., Wegelin, M., Gechter, D., Canonica, L. 2000. Nutzung von arsenhaltigem Grundwasser-katastrophale Folgen für Bangladesh. EAWAG News:18-20.

8. Jaspers, M. C. M., Suske, W. A., Schmid, A., Goslings, D. A. M., Kohler, H.-P. E., and Van der Meer J. R. 2000. HbpR, a new member of the XylR/DmpR subclass within the NtrC family of bacterial transcriptional activators, regulates expression of 2-hydroxybiphenyl metabolism in *Pseudomonas azelaica* HBP1. J. Bacteriol. 182:405-417.

9. Kaur P., and Rosen, B. P. 1992. Plasmid-encoded resistance to arsenic and antimony. Plasmid. 27:29-40.

10. Kuroda M., D. S., Sanders O. I., and Rosen B. P. 1997. Alternate energy coupling of ArsB, the membrane subunit of the Ars anion-translocating ATPase. J. Biol. Chem. 272: 326-331.

11. Lang, E., and Malik, K. A. 1996. Maintenance of biodegradation capacities of aerobic bacteria during long-term preservation. Biodegradation. 7:65-71.

12. Malik, K. A. 1988. A new freeze-drying method for the preservation of nitrogen-fixing and other fragile bacteria. Journal of Microbiological Methods. 8:259-271.

13. Malik, K. A., Beyersdorf-Radeck, B., and Schmid, R. D. 1993. Preservation of immobilized bacterial cell-matrix by drying for direct use in microbial sensors. World Journal of Microbiology and Biotechnology. 9:243-247.

14. McArthur, J. M., Ravenscroft, P., Safiullah, S., Thirlwall, M. F. 2000. Arsenic in groundwater: testing pollution mechanisms for sedimentary aquifers in Bangladesh. Water Resources Research. 37(1):109-117.

15. Miller, W. G., Leveau, J. H. J., and Lindow, S. E. 2000. Improved gfp and inaZ broad-host-range promoter-probe vectors. Molecular Plant-Microbe Interactions. 13:1243-1250.

16. Ramanathan, S., Shi, W., Rosen, B. P., and Daunert, S. 1998. Bacteria-based chemiluminescence sensing system using □-galactosidase under the control of the ArsR regulatory protein of the ars operon. Analytica Chimica Acta. 369:189-195.

17. Ramanathan, S., Shi, W., Rosen, B. P., and Daunert, S. 1997. Sensing antimonite and arsenic at the subattomole level with genetically engineered bioluminescent bacteria. Anal. Chem. 69:3380-3384.

18. Sambrook, J., Fritsch, E. F., and Maniatis, T. 1989. Molecular cloning: a laboratory manual., 2nd ed. Cold Spring Harbor Laboratory Press, N.Y.

19. Scott, D. L., Ramanathan, S., Shi, W., Rosen, B. P., and Daunert, S. 1997. Genetically engineered bacteria: electrochemical sensing systems for antimonite and arsenite. Anal. Chem. 69:16-20.

20. Silver, S., Misra, T. K. 1988. Plasmid-mediated heavy metal resistances. Ann. Rev. Microbiol. 42:717-43.

21. Sticher, P., Jaspers, M. C. M., Stemmler, K., Harms, H., Zehnder, A. J. B., and van der Meer, J. R. 1997. Development and characterization of a whole-cell bioluminescent sensor for bioavailable middle-chain alkanes in contaminated groundwater samples. Appl. Environ. Microbiol. 63:4053-4060.

22. Tauriainen, S., Virta, M., Chang, W., and Karp, M. 1999. Measurement of firefly luciferase reporter gene activity from cells and lysates using *Escherichia coli* arsenite and mercury sensors. Anal. Biochem. 272:191-198.

23. Tauriainen, S., Karp, M., Chang, W., and Virta, M. 1997. Recombinant luminescent bacteria for measuring bioavailable arsenite and antimonite. Appl. Environ. Microbiol. 63:4456-4461.

The invention claimed is

1. A biologically based test system for detection of an inorganic pollutant selected from the group consisting of arsenite, arsenate and antimonite in water samples, comprising a genetically modified bacterium producing a marker protein upon induction of a regulatory protein, wherein activity of said regulatory protein is induced by said pollutant, wherein said regulatory protein is ArsR, wherein said genetically modified bacterium comprises a first DNA binding site for said regulatory protein positioned in front of a gene encoding said regulatory protein and a second DNA binding site for said regulatory protein positioned between the gene encoding said regulatory protein and a gene encoding said marker protein, and wherein said marker protein is selected from the group consisting of alkaline phosphatase (PhoA), chloramphenicol acetyl transferase (CAT-gene), catechol dioxygenase (XylE), bacterial luciferase (LuxAB), eukaryotic luciferase (Luc) beta-galactosidase (LacZ), and green fluorescent protein (GEP).

2. The biologically based test system according to claim 1, wherein the genetically modified bacterial strain is selected from the group comprising the bacteria *Ralstonia metallidurens, Pseudomonas aeruginosa, Staphylococcus aureus* and *Eseherichia coli*.

3. The biologically based test system according to claim 2, wherein the genetically modified bacterial strain is the K12 strain of *E. coli*.

4. The biologically based test system according to claim 1, wherein the marker protein is bacterial luciferase or beta-galatosidase.

5. The biologically based test system according to claim 1, wherein genes for the regulatory protein as well as for the marker protein, and at least one additional DNA binding site for the regulatory protein, are located on a chromosome or on a bacterial plasmid.

6. The biologically based test system according to claim 5, wherein the bacterial plasmid is *E. coli* K12 plasmids pBR322, pUC 18, pACYC184 or RSF1010.

7. The genetically modified bacterial cells according to claim 2 for use in a biologically based test system for detection of an inorganic pollutant selected from the group consisting of arsenite, arsenate and antimonite in water samples, comprising a genetically modified bacterium producing a marker protein upon induction of a regulatory protein, wherein activity of said regulatory protein is induced by said pollutant, wherein said regulatory protein is ArsR, and wherein said genetically modified bacterium comprises a first DNA binding site for said regulatory protein positioned in front of a gene encoding said marker regulatory protein and a second DNA binding site for said regulatory protein positioned between the gene encoding said regulatory protein and the a gene encoding said marker protein, and wherein said marker protein is selected from the group consisting of alkaline phosphatase (PhoA), chloramphenicol acetyl transferase (CAT-gene), catechol dioxygenase (XylE), bacterial luciferase (LuxAB), eukaryotic luciferase (Luc) beta-galactosidase (LacZ), and green fluorescent protein (GEP).

8. The plasmids according to claim 6 for use in a biologically based test system for detection of an inorganic pollutant selected from the group consisting of arsenite, arsenate and antimonite in water samples, comprising a genetically modified bacterium producing a marker protein upon induction of a regulatory protein, wherein activity of said regulatory protein is induced by said pollutant; wherein said regulatory protein is ArsR, and wherein said genetically modified bacterium comprises a first DNA binding site for said regulatory protein positioned in front of a gene encoding said marker regulatory protein and a second DNA binding site for said regulatory protein positioned between a the gene encoding said regulatory protein and the a gene encoding said marker protein, and wherein said marker protein is selected from the group consisting of alkaline phosphatase (PhoA), chloramphenicol acetyl transferase (CAT-gene), catechol dioxygenase (XylE), bacterial luciferase (LuxAB), eukaryotic luciferase (Luc) beta-galactosidase (LacZ), and green fluorescent protein (GFP).

9. A biologically based test kit based on the test system according to claim 1, wherein said test kit comprises a colorimetric paper strip comprising genetically modified bacteria.

10. The biologically based test kit according to claim 9, wherein the genetically modified bacteria are selected from the group consisting of *Ralstonia metallidurens, Pseudomonas aeruginosa, Staphylococcus aureus* and *Escherichia coli*.

11. The method for producing a biologically based test kit according to claim 10, comprising the following steps:
   i. cultivating the bacterial cells, wherein the bacterial cells are comprised of *E. coli* K12 plasmids pBR322, pUC 18, pACYC 184 or RSF 1010;
   ii. mixing the bacterial cells with substances for drought protection;
   iii. transferring 5 to 20 microliters of the bacteria suspension of step (ii) on paper strips;
   iv. placing the paper strips in sterile tubes; and
   v. drying the paper strips under constant temperature and gradually lowered vacuum.

12. The method for producing a biologically based test kit according to claim 10, comprising the following steps:
   i. cultivating the bacterial cells, wherein the bacterial cells are comprised of *E. coli* K12 plasmids pBR322, pUC18, pACYC184 or RSF1010;
   ii. mixing the bacterial cells with substances for drought protection;
   iii. transferring 10 microliters of the bacteria suspension of step (ii) on paper strips;
   iv. placing the paper strips in sterile tubes; and
   v. drying the paper strips under constant temperature and gradually lowered vacuum.

13. A biologically based test kit based on the test system according to claim 1, wherein said test kit comprises a multi-well plate coated with bacteria selected from the group consisting of *Ralstonia metallidurens, Pseudomonas aeruginosa, Staphylococcus aureus* and *Escherichia coli*.

14. A method for producing a biologically based multi-well test kit according to claim 13, comprising the following steps:
   i. cultivating the bacterial cells, wherein bacterial cells are comprised of *E. coil* K12 plasmids pBR322, pUC18, pACYC184 or RSF1010;
   ii. mixing the bacterial cells with substances for drought protection;
   iii. transferring 30 to 70 microliters of the bacteria suspension of step (ii) into a glass vial or multi-well plate; and
   iv. drying the bacterial suspension under constant temperature and gradually lowered vacuum.

15. A method for producing a biologically based multi-well test kit according to claim 13, comprising the following steps:
   i. cultivating the bacterial cells, wherein bacterial cells are comprised of *E. coli* K12 plasmids pBR322, pUC18, pACYC184 or RSF1010;
   ii. mixing the bacterial cells with substances for drought protection;
   iii. transferring 50 microliters of the bacteria suspension of step (ii) into a glass vial or multi-well plate; and
   iv. drying the bacterial suspension under constant temperature and gradually lowered vacuum.

16. A method for the detection of arsenite and arsenate comprising employing the biologically based test kit of claim 10, wherein said test kit comprises a multi-well plate coated with the bacteria.

* * * * *

UNITED STATES PATENT AND TRADEMARK OFFICE
CERTIFICATE OF CORRECTION

PATENT NO. : 7,625,744 B2
APPLICATION NO. : 10/515877
DATED : December 1, 2009
INVENTOR(S) : Van Der Meer It is certified that error appears in the above-identified patent and that said Letters Patent is hereby corrected as shown below:

Title page, Item (75) Inventor, "Dübendorf" should read -- Lausanne --

Column 14, Line 39, Claim 1, "(GEP)" should read -- (GFP) --

Column 15, Line 4, Claim 7, "between a the gene" should read -- between a gene --

Column 15, Line 4, Claim 7, "and the a gene" should read -- and a gene --

Column 15, Line 10, Claim 7, "(GEP)" should read -- (GFP) --

Column 15, Line 22, Claim 8, "between a the gene" should read -- between a gene --

Column 15, Line 23, Claim 8, "between the a gene" should read -- between a gene --

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,625,744 B2 Page 1 of 1
APPLICATION NO. : 10/515877
DATED : December 1, 2009
INVENTOR(S) : Jan Roelof Van Der Meer It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 897 days.

Signed and Sealed this

Twenty-first Day of December, 2010

David J. Kappos
*Director of the United States Patent and Trademark Office*